United States Patent [19]

Horn et al.

[11] Patent Number: 5,475,161
[45] Date of Patent: Dec. 12, 1995

[54] PROCESS FOR THE PREPARATION OF ALCOHOLS IN TWO STAGES

[75] Inventors: Gerhardt Horn, Oberhausen; Carl D. Frohning, Wesel; Hans Liebern, Müheim/Ruhr; Wolfgang Zgorzelski, Oberhausen, all of Germany

[73] Assignee: Hoechst Aktiengesellschaft, Germany

[21] Appl. No.: 824,745

[22] Filed: Jan. 17, 1992

Related U.S. Application Data

[63] Continuation of Ser. No. 589,373, Sep. 27, 1990, abandoned.

[30] Foreign Application Priority Data

Sep. 28, 1989 [DE] Germany .................... 39 32 331.5

[51] Int. Cl.$^6$ ................ C07C 31/02; C07C 29/136; C07C 29/14
[52] U.S. Cl. ............................. 568/881; 568/883
[58] Field of Search ..................... 568/881, 883

[56] References Cited

U.S. PATENT DOCUMENTS 3,591,656  7/1971  Kroll ....................... 568/881
3,978,149  8/1976  Mertzweiller et al. ........... 585/277
4,684,750  8/1987  Kessen et al. ................ 568/883

FOREIGN PATENT DOCUMENTS 338045  3/1976  Switzerland .

Primary Examiner—Rebecca Cook
Attorney, Agent, or Firm—Jordan B. Bierman; Bierman and Muserlian

[57] ABSTRACT

A process for the preparation of alcohols by reaction of organic carbonyl compounds with hydrogen in two stages at elevated temperature and, optionally, elevated pressure. In the first stage, hydrogen and the carbonyl compounds are fed as a gas to a copper-containing catalyst and reacted to 80 to 99.5 percent of the theoretical conversion. In the second stage, the reaction product of the first stage is fed to a nickel/alumina/zirconium dioxide catalyst as a liquid, along with hydrogen. The carbonyl compounds used include aldehydes and their derivatives and, in particular, aliphatic unsaturated and saturated aldehydes.

20 Claims, No Drawings

PROCESS FOR THE PREPARATION OF ALCOHOLS IN TWO STAGES

This application is a continuation, of application Ser. No. /589,373 filed Sep. 27, 1990, now abandoned.

This application claims the priority of German Application P 3,932,331.5 filed Sep. 28, 1989.

The present invention relates to a two-stage process for the preparation of alcohols from organic carbonyl compounds. Organic carbonyl compounds are reacted with hydrogen at elevated temperature and, if appropriate at elevated pressure, in the presence of a hydrogenation catalyst in two or more stages to give the corresponding alcohols. In each of these stages, the reaction can be carried out batchwise or continuously, in either homogeneous or heterogeneous phases. Accordingly, the hydrogenation catalyst is present in a desolved from, as a finely divided suspension, or in lump form as a fixed-bed catalyst. In prior art methods the carbonyl compounds to be hydrogenated can be added to the catalyst as either a gas or a liquid. According to the invention, the carbonyl compounds are reacted in a first stage as a gas and in a second stage as a liquid. The inventive catalyst employed in the first stage is a copper-containing hydrogenation catalyst, while the second stage reaction is conducted in the presence of a nickle/alumina/zirconium dioxide catalyst.

BACKGROUND OF THE INVENTION

A comprehensive review of the preparation of alcohols by catalyst hydrogenation of carbonyl compounds, and particularly of ketones, aldehydes and derivatives thereof, can be found in Houben-Weyl, Methoden der Organischen Chemie (Methods of Organic Chemistry), Georg Thieme Verlag Stuttgart-New York 1984, volume VI/1 pages 9 to 111.

DE-AS 1,227,882 describes a two- or three-stage hydrogenation of unsaturated aldehydes in the gas phase, in which the first stage is conducted in the presence of a copper catalyst while the second stage employs a palladium catalyst or a supported nickel catalyst. In the third stage, a palladium catalyst is used.

DE-AS 1,276,618 relates to a two-stage hydrogenation of saturated and unsaturated aldehydes in the gas phase, in which the reaction first takes place on a copper/nickel catalyst and then on a nickel and/or palladium catalyst.

For preparing 2-ethylhexanol from propylene, DE 3,530,839 Al describes a two-stage hydrogenation of 2-ethylhexenal, in which the reaction is first conducted in the gas phase using a copper catalyst and then in liquid phase using a nickel-containing catalyst.

The process processes describes above for preparing alcohols leave something to be desired, however as far as conversion and/or the selectivity of the catalytic hydrogenations is concerned. The relatively long reaction times lead to correspondingly low outputs at high reaction temperatures, particularly in the second stage. Further, the valuable product can, in most cases, be recovered from the reaction product by means of distillation in the desired purity, only at great expense.

DESCRIPTION OF THE INVENTION

There is, therefore, a demand for a process which eliminates the above-mentioned disadvantages. This object is achieved in the inventive process by reaction of organic carbonyl compounds at elevated temperature and, if appropriate, elevated pressure, with hydrogen in two stages. The organic carbonyl compounds are added as a gas to a copper-containing catalyst in the first stage and reacted with hydrogen to 80 to 99.5 percent of theoretical conversion. In the second stage, the reaction product of the first stage is added as a liquid to a nickel/zirconium dioxide-containing catalyst in the presence of hydrogen.

The process of the invention makes it possible to operate the hydrogenation in both stages at significantly higher flow rates compared to known processes. At the same time, it insures that the overall reaction proceeds at a very high conversion and selectivity. Furthermore, the hydrogenation in the second stage can be carried out at relatively low temperatures despite the higher proportion of carbonyl compounds which remain unconverted after the first stage. The reaction product which is obtained can be converted into a final product of high purity with a comparatively small outlay in terms of distillation.

The inventive process can be applied to the conversion of ketones, aldehydes, and derivatives thereof. Ketones which can be used include acetone, methyl ethyl ketone, diethyl ketone, hexanones (e.g. cyclohexanone, heptanones, octanones), higher ketones and aromatic ketones (such as acetophenone and benzophenone). Ketone derivatives include acetol (hydroxyacetone), acetoin (acetylmethylcarbinol), dihydroxyacetone, benzoin, lactones, and ketoses, such as fructose.

The inventive process can also be used to react aromatic, araliphatic, cycloaliphatic, aliphatic aldehydes, and derivatives thereof, in particular cycloaliphatic, aliphatic aldehydes and derivatives thereof. Aliphatic aldehydes and derivatives thereof are preferred; of these, the use of saturated and unsaturated, normal and iso, aliphatic aldehydes of 2 to 18 carbon atoms are especially suitable. Acetaldehyde, propanal, n- and i-butanal, n- and i-pentanal, n- and i-octanal, n- and i-nonanal and alkanals of 11 to 18 carbon atoms are preferred. Most preferably, propanal, n- and i-butanal, and n- and i-octanal are recommended. With the exception of acetaldehyde, these aldehydes can be prepared, for example, by hydroformylation of olefins or aldol condensation of two identical or different aldehydes. They can be used in the process according to the invention in previously purified form, but can also be employed as a crude reaction mixture.

Unsaturated aldehydes are also useful. They include acrolein, crotonaldehyde, methacrolein, ethylacrolein, propylacrolein, heptenal, octenal and 2-ethylhexanol. The process is particularly suitable for crotonaldehyde, and 2-ethylhexanol, and most preferably for 2-ethylhexenal.

The procedure according to the invention is particularly adapted to a continuous process. The feed material containing the carbonyl compounds is heated in an evaporator and fed to the first stage as a gas, together with hydrogen. The copper-containing catalyst is advantageously in lump form. Usually, it is arranged as a layer in an upright tubular reactor which is equipped with cooling and heating means. The feed material and hydrogen can be passed through the catalyst layer either from bottom to top or (preferably) from top to bottom.

The reaction is carried out at 100° to 200° C., preferably 120° to 180° C., and most preferably 140° to 160° C.; and at 0.05 to 2.0 MPa, in particular 0.1 to 1.2 MPa, and preferably at 0.15 to 1.0 MPa. Temperature and pressure also depend on the type of feed material. Reactive carbonyl compounds, for example, will react at relatively low temperatures of 100° to 130° C., while inert carbonyl compounds require higher temperatures of about 150° to 180° C.

A temperature range of 140° to 160° C. has been proven to be suitable for most cases. The reaction temperature is also influenced by the service life of the catalyst. Thus, a fresh, unused catalyst makes it possible to react the carbonyl compounds at lower temperatures (130° to 145° C.), while a used catalyst, as a function of the service life, generally requires higher temperatures (150° C., and particularly above 155° C.), for hydrogenation to occur.

The copper-containing catalyst used in the first stage contains 15 to 85, preferably 30 to 80 and, most preferably, 50 to 70 percent by weight of copper; 0.2 to 20, preferably 1.0 to 10 and, most preferably, 2 to 8 percent by weight of MgO; 0.03 to 12, preferably 0.5 to 8, and, most preferably, 1 to 5 percent by weight of $Cr_2O_3$; and 5 to 80, preferably 7 to 60 and, most preferably, 9 to 50 percent by weight of $SiO_2$ as a support. In each case percentages are based on the total composition of the catalyst.

An important feature of the inventive process is that, in the first stage, all the carbonyl compounds are not fully converted. Instead, only most of the carbonyl is reacted so that, in the second stage, a portion of the carbonyl compound remains to be converted to the corresponding alcohol. In the first stage, 80 to 99.5, preferably 90 to 99, and most preferably 93 to 98 percent of the carbonyl compounds are converted. The degree of conversion depends on the type of feed material, the particular activity of the catalyst, the temperature, and the desired flow rate.

The amount of hydrogen used must, at least, correspond to the stoichiometry of the reaction. However, usually a stoichiometric excess of hydrogen is used to shift the reaction in the desired direction. A hydrogen excess of 0.5 to 50, particularly 1 to 20, and preferably 2 to 10 mol per equivalent of carbonyl compound has proven to be sufficient for the gas phase hydrogenation in the first stage. Unconverted hydrogen can be recycled into the reaction. The reaction mixture leaving the first stage is condensed and, if desired, the hydrogen is separated. It can be fed to the second stage directly or after intermediate storage.

In the second stage, the hydrogenation is carried out in liquid phase, over a supported catalyst containing nickel, alumina, and zirconium dioxide as coprecipitates. The catalyst can be used either in a finely divided suspension or as a fixed-bed catalyst in granular form. The reaction temperature is 60 to 150, in particular 80 to 140, preferably 90 to 130 and, most preferably, 100° to 125° C. A pressure of 0.1 to 25 MPa, advantageously 1.0 to 15 MPa, and preferably 2.0 to 10 MPa is used. As with the first stage, precise reaction conditions, including temperature and the pressure, depend on the type of feed material, the residual content of carbonyl compound, the activity of the catalyst, and the desired flow rate.

Reactive carbonyl compounds can be hydrogenated at comparatively low reaction temperatures of 60° to 120° C., whereas inert carbonyl compounds require higher temperatures, for example 100° to 150° C. A temperature range from 100° to 125° C. has proven to be suitable for most cases. The reaction temperature is also influenced by the service life of the catalyst. Thus, a fresh, unused catalyst makes it possible to react the carbonyl compounds at low temperatures, for example 80° to 125° C. A used catalyst, as a function of its service life, generally requires higher temperatures, for example above 110, in particular above 115, and preferably above 125° C., for the hydrogenation to take place.

The liquid carbonyl compound and hydrogen reactants can be fed, either batchwise or continuously, to the catalyst, which is preferably suspended in finely divided form. Alternatively, the feed material containing the carbonyl compound can be passed, together with hydrogen, concurrently or countercurrently over the supported, granulated nickel/alumina/zirconium dioxide catalyst arranged as a fixed bed. In the industrial practice of the inventive process, the fixed-bed procedure is often preferable, the feed mixture being passed over the fixed catalyst either from top to bottom (downward flow procedure) or from bottom to top (liquid-phase procedure). If the downward flow procedure is used, the hydrogen is passed over the granular, fixed supported catalyst concurrently or countercurrently, preferably concurrently, relative to the feed material. If the liquid-phase procedure is employed, the hydrogen is advantageously passed over the granular fixed support catalyst concurrently relative to the feed mixture.

The minimum amount of hydrogen must correspond to the stoichiometry of the reaction. However, as a rule, a stoichiometric excess of hydrogen is used to influence the reaction in an advantageous manner. A hydrogen excess of 1 to 100, particularly 2 to 50, and preferably 5 to 10 mol per equivalent of carbonyl compound is sufficient for carrying out the hydrogenation in liquid phase. Unconverted hydrogen can be recycled.

The hydrogenation catalyst used in the second stage contains 20 to 90 percent by weight of nickel, based on the total catalyst. It also contains 1 to 30, advantageously 3 to 15, and preferably 4 to 10 parts by weight of alumina; and 0.5 to 20, in particular 1 to 10, and preferably 1.5 to 5 parts by weight of zirconium dioxide, the amounts in each case being relative to 100 parts by weight of nickel as a coprecipitate on the support material.

Since this specific catalyst is important in carrying out the second stage of the inventive process, one method of the preparation thereof will be described in more detail. An aqueous Ni—Al—Zr mixed salt solution is precipitated by the addition of an aqueous solution of a basic compound. The basic compound is employed in a stoichiometric excess of 5 to 100 percent, based on the amount necessary for quantitative precipitation of Ni, Al and Zr. Ni, Al and Zr are simultaneously precipitated at 60° to 120° C. and a pH of 7 to 10, and deposited as coprecipitates on a support material.

In order to prevent hydrolysis, which is an undesired reaction, and influence the precipitation in an advantageous manner, it is recommended that an excess of free acid be added to the mixed salt solution in an $H+:Zr^{4+}$ ratio of 2 to 40:1, advantageously 3 to 30:1, and preferably 4 to 20:1. The amount of free acid is determined by titration with NaOH (end point at pH 0.8). Hydrochloric acid, sulfuric acid, and preferably nitric acid can be used as the free acid.

The mixed salt solution consists of 10 to 100, advantageously 20 to 80, and preferably 30 to 50 g of Ni/liter. It contains aluminum in an amount of 1 to 30, in particular 3 to 15, and preferably 4 to 10 parts by weight of $Al_2O_3$ per 100 parts by weight of Ni. Furthermore, it contains zirconium in an amount of 0.5 to 20, advantageously 1 to 10, and preferably 1.5 to 5 parts by weight of $ZrO_2$ per 100 parts by weight of Ni. The mixed salt solution is prepared by dissolving water-soluble inorganic, organic or complex salts of nickel, zirconium, and aluminum in water. In particular the sulfates, chlorides, acetates, nitrates and, most preferably, the nitrates are used.

The precipitant is an aqueous solution of a basic compound, in particular an aqueous solution of alkali metal carbonate, alkali metal bicarbonate, alkali metal hydroxide, ammonium hydroxide, or ammonium carbonate. The aqueous solution has a pH of 7.5 to 13, preferably 8 to 12, and most preferably 9 to 11. Good results are obtained with aqueous solutions containing 0.3 to 1.5, and preferably 0.8 to 1.2 mol of alkali metal carbonate/liter of solution.

To insure the complete precipitation of a particularly homogeneous coprecipitate, the basic compound is used in a stoichiometric excess of 50 to 100 percent, advantageously 10 to 70 percent, preferably 20 to 40 percent, based on the amount of basic compound necessary for the complete precipitation of Ni, Al, and Zr. The precipitation is effected by either continually combining the mixed salt solution with the precipitant and mixing them or, in a preferred variation, by initially introducing the precipitant and passing the mixed salt solution into the precipitant.

The support material can be used in the reaction together with the mixed salt solution and/or the precipitant. It is particularly advantageous to first mix the mixed salt solution and the precipitant with one another before adding the support material. Suitable support materials are activated carbon, clay, pumice, $\gamma$-$Al_2O_3$, $SiO_2$, silica gel, kieselguhr and siliceous earth, in particular, $SiO_2$, silica gel, kieselguhr and siliceous earth. Preferably, kieselguhr and $SiO_2$ in the form of precipitated silica are used.

Usually, 6 to 80, in particular 15 to 65, and preferably 35 to 50 parts by weight of support material are used per 100 parts by weight of Ni. For the purpose of preparing a homogeneous coprecipitate, a pH range of 7 to 10, in particular 7.3 to 9, and preferably 7.5 to 8.5 is maintained along with a temperature of 60° to 120° C., advantageously 70 to 110, and preferably 95° to 105° C., during the precipitation.

After precipitation is complete, and optionally after cooling, the product is filtered, washed, shaped if necessary, dried, and reduced. Drying is carried out at a temperature of 40° to 120° C., preferably at 50° to 100° C. Reduction is carried out at 300° to 550° C. A degree of reduction of at least 80 percent, preferably at least 90 percent, and most preferably at least 95 percent is desirable. The degree of reduction is undertood to mean the ratio of the amount of nickel metal to the total amount of nickel times 100 percent.

In the second stage, the portion of the carbonyl compounds which are not converted in the first stage are reacted to give corresponding alcohols at a high flow rate by means of the supported nickel, alumina, and zirconium dioxide catalyst described above.

The inventive process can generally be operated at higher outputs than is possible with prior art methods. The feed material containing the carbonyl compounds is fed into the first stage at a space velocity (volume of liquid feed material/volume of catalyst per hour=V/Vh) of 0.3 to 2.0, preferably 0.5 to 1.8 and, most preferably, 0.6 to 1.5. The space velocity in the second stage is 0.5 to 2.5, preferably 0.7 to 1.8 and, most preferably, 0.8 to 1.5.

The space velocity selected in the first stage affects the space velocity desirable in the second stage and vice versa. If a high space velocity has been selected in the first stage, for example 1.5 to 2.0, the second stage should be operated at a suitably adjusted space velocity, for example 0.5 to 1.0, in order to insure the highest possible yield of valuable product. The higher the space velocity is in the first stage, the lower it should be in the second stage. Conversely, an increased space velocity in the second stage requires a correspondingly reduced space velocity in the first stage.

Space velocity also depends on the feed material. In general, saturated carbonyl compounds, in particular aldehydes, can be reacted at higher space velocities, while unsaturated carbonyl compounds, in particular aldehydes, require a somewhat reduced space velocity. Thus, when n-butanal is used, the space velocity in the first stage should be 0.6 to 2.4, advantageously 0.8 to 1.8 and, in the second stage, 0.7 to 2.0, preferably 0.9 to 1.7. When 2-ethylhexane is used, the space velocity should be 0.4 to 2.0, preferably 0.5 to 1.8 in the first stage and 0.6 to 1.8 and, for best results, 0.8 to 1.6, in the second stage.

The examples described below are supplied to further illustrate the invention but the invention is in no way limited to these specific embodiments.

EXAMPLE 1

1st stage

A 1000 ml bed of a catalyst in pellet form containing, in its activated state, 80 percent by weight of Cu, 4.0 percent by weight of MgO, 2.0 percent by weight of $Cr_2O_3$ and 12 percent by weight of $SiO_2$, as a support, is placed in a vertical tube. The feed material to be reacted is fed as a liquid to an evaporator and then passed, as a gas, together with hydrogen, over the catalyst bed.

| | Reaction conditions | |
|---|---|---|
| Feed material: | 1600 ml of 2-ethylhexenal per hour | |
| Composition: | Forerun | 0.6% by weight |
| | 2-Ethylhexenal | 98.9% by weight |
| | 2-Ethylhexanal | —% by weight |

2nd stage

The gaseous reaction mixture leaving the first stage is condensed and further processed as a liquid. A 1000 ml catalyst bed, in pellet form, containing 100 parts by weight of Ni, 5 parts by weight of alumina, and 3 parts by weight of zirconium dioxide as coprecipitates, and 40 parts by weight of $SiO_2$, as a support, is packed in a vertical tube. The reaction mixture originating from the first stage is passed, as a liquid, through the catalyst bed from top to bottom (downward flow procedure).

| | Reaction conditions | |
|---|---|---|
| Feed material: | 900 ml of the reaction mixture from the first stage per hour | |
| Composition: | Forerun | 0.4% by weight |
| | 2-Ethylhexenal | 8.0% by weight |
| | 2-Ethylhexanal | 0.6% by weight |
| | 2-Ethylhexanol | 90.9% by weight |
| | Higher boiling component | 0.2% by weight |
| | CO number | 35.4 (mg of KOH/g) |
| | Iodine number | 18.3 (g of $I_2$/100 g) |
| | 2-Ethylhexanol | —% by weight |
| | Higher boiling component | 0.5 |
| | CO number | 434 (mg of KOH/g) |
| | Iodine number | 226 (g of $I_2$/100 g) |
| Hydrogen: | 2400 Nl of $H_2$ per hour | |
| V/Vh*: | 1.6 | |
| Pressure: | 0.2 MPa | |
| Temperature: | 145° C. | |
| Conversion: | 92%, based on aldehyde | |
| | 91%, based on C—C double bond | |
| 2nd stage | | |
| Hydrogen: | 120 Nl of $H_2$ per hour | |
| V/Vh*: | 0.9 | |
| Pressure: | 2.5 MPa | |
| Temperature: | 125° C. | |

-continued

| Reaction conditions | |
|---|---|
| Conversion: | >99.9%, based on aldehyde |
| | >99.9%, based on C—C double bond |
| | CO number: <0.05 (mg of KOH/g) |
| | Iodine number: <0.03 (g of I$_2$/100 g) |

*Space velocity (volume of liquid feed material/volume of catalyst × hour)

EXAMPLE 2

1st stage

In the first stage, Example 1 is repeated, except that the amount of feed material is changed.

| Reaction conditions | |
|---|---|
| Feed material: | 900 ml of 2-ethylhexenal per hour |
| Composition: | see Example 1 |
| Hydrogen: | 2400 Nl of H$_2$ per hour |
| V/Vh: | 0.9 |
| Pressure: | 0.2 MPa |
| Temperature: | 145° C. |
| Conversion: | 99%, based on aldehyde |
| | 98%, based on C—C double bond |

2nd stage

In the 2nd stage, Example 1 is repeated, except that the amount of feed material is changed.

| Reaction conditions: | | |
|---|---|---|
| Feed material: | 1600 ml of the reaction mixture from the first stage per hour | |
| Composition: | Forerun | 0.1% by weight |
| | 2-Ethylhexanol | 96.6% by weight |
| | 2-Ethylhexanal | 1.0% by weight |
| | 2-Ethylhexenal | 2.0% by weight |
| | Higher boiling component | 0.3% by weight |
| | CO number | 4.4 (mg of KOH/g) |
| | Iodine number | 4.5 (g of I$_2$/100 g) |
| Hydrogen: | 120 Nl of H$_2$ per hour | |
| V/Vh: | 1.6 | |
| Pressure: | 2.5 MPa | |
| Temperature: | 125° C. | |
| Conversion: | >99.9%, based on aldehyde | |
| | >99.9%, based on C—C double bond | |
| | CO number: 0.04 (mg of KOH/g) | |
| | Iodine number: <0.03 (g of I$_2$/100 g) | |

EXAMPLE 3

1st stage

In the 1st stage, Example 1 is repeated, except that n-butanal is used as feed material.

| Reaction conditions | | |
|---|---|---|
| Feed material: | 1500 ml of n-butanal per hour | |
| | Forerun | 0.3% by weight |
| | n-Butanal | 99.2% by weight |
| | n-Butanol | —% by weight |
| | Higher boiling component | 0.5% by weight |
| | CO number | 776 (mg of KOH/g) |
| Hydrogen: | 2400 Nl of H$_2$ per hour | |
| V/Vh: | 1.5 | |
| Pressure: | 0.2 MPa | |
| Temperature: | 145° C. | |
| Conversion: | 94%, based on aldehyde | |
| | CO number 46.6 (mg of KOH/g) | |

2nd stage

In the 2nd stage, Example 1 is repeated, except that the reaction mixture obtained by reaction of n-butanal in the first stage is used as feed material.

| Reaction conditions | | |
|---|---|---|
| Feed material: | 1000 ml of reaction mixture from the first stage per hour | |
| Composition: | Forerun | 0.5% by weight |
| | n-Butanal | 5.9% by weight |
| | n-Butanol | 93.2% by weight |
| | Higher boiling component | 0.1% by weight |
| | CO number | 46.6 (mg of KOH/g) |
| Hydrogen: | 100 Nl of H$_2$ per hour | |
| V/Vh: | 1.0 | |
| Pressure: | 8.0 MPa | |
| Temperature: | 115° C. | |
| Conversion: | >99.9%, based on aldehyde | |
| | CO number ≦0.7 (mg of KOH/g) | |

EXAMPLE 4

1st stage

In the 1st stage, Example 3 is repeated, except that the amount of feed material is changed.

| Reaction conditions | |
|---|---|
| Feed material: | 900 ml of n-butanal per hour |
| Composition: | as in Example 3 |
| Hydrogen: | 2400 Nl of H$_2$ per hour |
| V/Vh: | 0.9 |
| Pressure: | 0.2 MPa |
| Temperature: | 145° C. |
| Conversion: | 98.4%, based on aldehyde |
| | CO number 12.4 (mg of KOH/g) |

2nd stage

In the 2nd stage, Example 3 is repeated, except that the reaction mixture obtained from the reaction of n-butanal in the first stage is used as feed material.

| Reaction conditions | | |
|---|---|---|
| Feed material: | 1700 ml of the reaction mixture from the first stage per hour | |
| Composition: | Forerun | 0.2% by weight |
| | n-Butanal | 1.6% by weight |
| | n-Butanol | 98.0% by weight |
| | Higher boiling component | 0.1% by weight |
| | CO number | 12.4 (mg of KOH/g) |
| Hydrogen: | 120 Nl of H$_2$ per hour | |
| V/Vh: | 1.7 | |
| Pressure: | 2.5 MPa | |
| Temperature: | 125° C. | |

| Reaction conditions | |
|---|---|
| Conversion: | ≧99.9%, based on aldehyde<br>CO number ≦0.7 (mg of KOH/g) |

Comparative Example 1

1st stage
The procedure of the 1st stage of Example 2 is repeated.

| Reaction conditions | |
|---|---|
| Feed material: | 900 ml of 2-ethylhexenal per hour |
| Composition: | see 1st stage of Example 1 |
| Hydrogen: | 2400 Nl of $H_2$ per hour |
| V/Vh: | 0.9 |
| Pressure: | 0.2 MPa |
| Temperature: | 145° C. |
| Conversion: | 99%, based on aldehyde<br>98%, based on C—C double bond<br>CO number: 4.4 (mg of KOH/g)<br>Iodine number: 4.5 (g of $I_2$/100 g) |

2nd stage
The procedure of the 2nd stage of Example 1 is repeated, except that the nickel catalyst contains only 55 percent by weight of Ni, 30 to 35 percent by weight of $SiO_2$, and neither alumina nor zirconium dioxide is included.

| Reaction conditions | | |
|---|---|---|
| Feed material: | 900 ml of the reaction mixture from the 1st stage per hour | |
| Composition: | Forerun | 0.1% by weight |
| | 2-Ethylhexanal | 1.0% by weight |
| | 2-Ethylhexenal | 2.0% by weight |
| | 2-Ethylhexanol | 96.6% by weight |
| | Higher boiling component | 0.3 |
| | CO number | 4.4 (mg of KOH/g) |
| | Iodine number | 4.5 (g of $I_2$/100 g) |
| Hydrogen: | 120 Nl of $H_2$ per hour | |
| V/Vh: | 0.9 | |
| Pressure: | 2.5 MPa | |
| Temperature: | 125° C. | |
| Conversion: | 99.4%, based on aldehyde<br>99.3%, based on C—C double bond<br>CO number 0.03<br>Iodine number 0.03 | |

Despite a reduced flow rate(V/Vh) compared with the 2nd stage of Example 1 and the 1st stage of Example 2, the final product obtained does not meet the quality of the final product obtained by the invention in Examples 1 and 2. While the reaction product of Examples 1 and 2 can be processed without any great effort to give a 2-ethylhexanol grade suitable for the preparation of plasticizers, this cannot be achieved with the reaction product of Comparative Example 1.

Comparative Example 2

1st stage
The procedure of the 1st stage of Example 4 is repeated.

| Reaction conditions | |
|---|---|
| Feed material: | 900 ml of n-butanal per hour |
| Composition: | as in the 1st stage of Example 3 |
| Hydrogen: | 2400 Nl of $H_2$ per hour |
| V/Vh: | 0.9 |
| Pressure: | 0.2 MPa |
| Temperature: | 145° C. |
| Conversion: | 98.4%, based on aldehyde<br>CO number 12.4 |

2nd stage
The procedure of the 2nd stage of Example 3 is repeated, except that the nickel catalyst contains only 55 percent by weight of Ni, about 30 to 35 percent by weight of $SiO_2$, and neither alumina nor zirconium dioxide is used.

| Reaction conditions | |
|---|---|
| Feed material: | 1000 ml of the reaction mixture from the 1st stage of Comparative Example 2 per hour |
| Hydrogen: | 100 Nl of $H_2$ per hour |
| V/Vh: | 1.0 |
| Pressure: | 8.0 MPa |
| Temperature: | 115° C. |
| Conversion: | 99.4%, based on aldehyde |

Compared with this example, the invention of Example 4 achieves a significant higher flow rate in the 2nd stage and, at the same time, results in a better conversion to the desired product.

What is claimed is:

1. A process for the preparation of alcohols by reaction of organic carbonyl compounds at elevated temperatures, said process comprising:
    feeding said organic carbonyl compounds as a gas to a copper-containing first catalyst in a first stage and reacting said compounds with hydrogen to 80 to 99.5 percent of theoretical to form a reaction product, and
    feeding said reaction product to a nickel/alumina/zirconium dioxide second catalyst on a support, as a liquid, and further reacting said reaction product with hydrogen.

2. The process of claim 1 wherein said carbonyl compounds are selected from the group consisting of ketones, ketone derivatives, aldehydes, and aldehyde derivatives.

3. The process of claim 2 wherein said carbonyl compounds are selected from the group consisting of aldehydes and aldehyde derivatives.

4. The process of claim 3 wherein said carbonyl compounds are selected from the group consisting of saturated and unsaturated aliphatic aldehydes.

5. The process of claim 3 wherein said carbonyl compounds are selected from the group consisting of n-butanal and 2-ethylhexenal.

6. The process of claim 1 wherein said copper-containing catalyst contains 15 to 85 percent by weight of copper, 0.2 to 20 percent by weight of MgO, 0.03 to 12 percent by weight of $Cr_2O_3$ and 5 to 80 percent by weight of $SiO_2$ as support, weights in each case being based on said catalyst.

7. The process of claim 1 wherein said process is conducted at an elevated pressure.

8. The process of claim 7 wherein, in said first stage, the temperature is 100° to 200° C. and the pressure is 0.05 to 2.0 MPa and, in the second stage, the temperature is 60° to 150° C. and the pressure is 0.1 to 25 MPa.

9. The process of claim 1 wherein 90 to 99.0 of said carbonyl compounds are converted in said first stage.

10. The process of claim 9 wherein 93 to 98 percent of said carbonyl compounds are converted in said first stage.

11. The process of claim 1 wherein said second catalyst comprises 20 to 90 percent by weight of nickel, 1 to 30 parts by weight of alumina and 0.5 to 20 parts by weight of zirconium dioxide, weights in each case being relative to 100 parts by weight of Ni as coprecipitate on a support material.

12. The process of claim 1 wherein said support comprises activated carbon, clay, pumice, $\gamma$-$Al_2O_3$, $SiO_2$, silica gel, kieselguhr and/or siliceous earth.

13. The process of claim 12 wherein said support is at least one material selected from the group consisting of $SiO_2$, silica gel, kieselguhr and siliceous earth.

14. The process of claim 13 wherein said support is at least one material selected from the group consisting of kieselguhr and $SiO_2$ in the form of precipitated silica.

15. The process of claim 1 wherein the supported catalyst contains 6 to 80 parts by weight of support material per 100 parts by weight of Ni.

16. The process of claim 15 wherein the supported catalyst contains 15 to 65 parts by weight of support material per 100 parts by weight of Ni.

17. The process of claim 16 wherein the supported catalyst contains 35 to 50 parts by weight of support material per 100 parts by weight of Ni.

18. The process of claim 1 wherein the space velocity expressed as the volume of liquid feed material to the volume of catalyst per hour (V/Vh) is 0.3 to 2.0 in the first stage and 0.5 to 2.5 in the second stage.

19. The process of claim 18 wherein said space velocity is 0.5 to 1.8 in said first stage and 0.7 to 1.8 in said second stage.

20. The process of claim 19 wherein said space velocity is 0.6 to 1.5 in said first stage and 0.8 to 1.5 in said second stage.

* * * * *